United States Patent [19]

Vasey et al.

[11] 4,160,115

[45] Jul. 3, 1979

[54] PROCESS FOR THE MANUFACTURE OF BUTENEDIOL

[75] Inventors: Charles H. Vasey; Dhafir Y. Waddan, both of Middlesbrough, England

[73] Assignee: Imperial Chemical Industries Limited, London, England

[21] Appl. No.: 939,917

[22] Filed: Sep. 5, 1978

[30] Foreign Application Priority Data

Sep. 22, 1977 [GB] United Kingdom ............... 39533/77
Jan. 23, 1978 [GB] United Kingdom ................. 2600/78

[51] Int. Cl.$^2$ ............................................. C07C 31/18
[52] U.S. Cl. ..................................................... 568/857
[58] Field of Search ......................................... 568/857

[56] References Cited

U.S. PATENT DOCUMENTS

| 2,555,927 | 6/1951 | Himel et al. ......................... 568/857 |
| 3,140,303 | 7/1964 | De La Mare et al. ............... 568/857 |

FOREIGN PATENT DOCUMENTS

2414341 10/1975 Fed. Rep. of Germany ........... 568/857
2421408 11/1975 Fed. Rep. of Germany.
2607039 9/1976 Fed. Rep. of Germany.

*Primary Examiner*—Joseph E. Evans
*Attorney, Agent, or Firm*—Cushman, Darby & Cushman

[57] ABSTRACT

Butenediol is obtained by reacting butadiene with water and oxygen in the presence of a copper, nickel, cobalt, chromium, manganese or molybdenum catalyst and preferably in the presence of carbon dioxide.

10 Claims, No Drawings

PROCESS FOR THE MANUFACTURE OF BUTENEDIOL

THIS INVENTION relates to the manufacture of butenediols and more particularly to the manufacture of 2-butene-1,4-diol.

It is known from German OLS No. 2,607,039 to react an aliphatic olefine, particularly a mono-olefine, containing 2 to 4 carbon atoms in an aqueous medium with copper or iron cations and bromine containing anions, optionally in the presence of molecular oxygen so as to produce vicinal glycols such as ethylene glycol and 1,2-propylene glycol. We have now found that when the olefine is butadiene the product of the reaction includes 2-butene-1,4-diol, that other cations may be used in the catalyst and that the reaction may be carried out in the presence of anions other than bromine containing anions.

According to our invention a process for the manufacture of 2-butene-1,4-diol comprises reacting butadiene with water and oxygen in the presence of a copper, nickel, cobalt, chromium, manganese or molybdenum catalyst.

The reaction is preferably effected in the presence of carbon dioxide and may be effected in either the liquid or the vapour phase.

At least 1 mole of water is used per mole of butadiene, but an excess may be used, for example up to 10 moles/mole.

The oxygen may be molecular oxygen as such or may be a molecular oxygen-containing gas consisting of a mixture of oxygen with another gas which does not interfere with the reaction, for example nitrogen or argon. Air may be used, as may mixtures of oxygen and nitrogen with a higher or lower oxygen content than that of air.

The carbon dioxide, when used, acts as a promoter and need not be used in equimolar amounts compared with that of the butadiene. Amounts of from 0.01 to 0.5 mols of carbon dioxide per mole of butadiene are convenient, although larger amounts are not deleterious and are not excluded.

The catalyst may be the metal or a metal compound or a mixture of the metal and a compound. The metal compound is particularly a salt, for example an inorganic salt such as a halide, for example chloride, bromide or iodide, or an organic acid salt, especially a carboxylate and particularly a salt of an aliphatic carboxylic acid having up to 20 preferably up to 6 carbon atoms. The metal in the metal compound may be in any of the possible valency states. Examples of suitable copper compounds are cuprous chloride, cuprous bromide, cupric acetate, cupric glycollate, cupric lactate and cuprous trifluormethane sulphonate.

Examples of suitable nickel compounds are nickel chloride, nickel bromide, nickel iodide and nickel acetate. Examples of suitable cobalt compounds are cobalt (II) chloride, cobalt (III) chloride, cobalt (II) bromide, cobalt (II) iodide, cobalt (II) acetate and cobalt (II) propionate.

Examples of suitable chromium compounds are chromium (II) chloride, chromium (III) chloride, chromium (III) bromide, chromium (III) iodide, chromium (II) acetate, chromium (III) acetate and chromium (III) acetoacetonate. Examples of suitable manganese compounds are manganese dichloride, manganese trichloride, manganese dibromide, manganese diiodide, manganese (II) benzoate, manganese (II) lactate, manganese (II) tartrate. Examples of suitable molybdenum compounds are molybdenum di-, tri-, tetra- and pentachlorides, molybdenum di- and tetra- bromides, molybdenum di- and tetra-iodides and molybdenum hexacarbonyl.

It is also advantageous to carry out the reaction in the presence of lithium hydroxide.

When the reaction is effected in the liquid phase it is conveniently carried out in the presence of a solvent. The solvent is preferably water-miscible. Suitable solvents are, for example, lower (eg. $C_1$ to $C_6$) aliphatic alcohols, lower (eg. $C_1$ to $C_6$) aliphatic ketones and lower (eg. $C_1$ to $C_6$)alkyl cyanides, for example ethanol, n-propanol, isopropanol, butanols, especially t-butanol, butenediol, acetone, methyl ethyl ketone, methyl isobutyl ketone and acetonitrile. Compounds may be added which may assist the solubility of the butadiene and/or the catalyst in the water used in the reaction. Such compounds are, for example, organic sulphur compounds, for examply crotyl phenyl sulphide and triphenyl thiophosphite.

The reaction is best carried out at a raised temperature, for example at a temperature within the range 50° to 150° C., preferably 80° to 130° C. The reaction may be conveniently carried out, for example, by adding butadiene, water, solvent and catalyst, and optionally carbon dioxide, to an autoclave, pressurising the autoclave with oxygen and heating the autoclave to the appropriate temperature for the desired time. The time of reaction may be varied according to the degree of conversion desired, and may vary, for example, from 0.5 hour up to 50 hours. The butenediol product may be separated from the reaction mixture, for example by fractional distillation. Unconverted materials may be recycled.

The product consists of a mixture of cis- and trans-2-butene-1,4-diol with some butene-3,4-diol. The product may be used as an intermediate in the manufacture of tetrahydrofuran, in the manufacture of polyurethanes, and for conversion to butane-1,4-diol useful in the manufacture of polyesters.

The invention is illustrated but not limited by the following Examples in which the parts and percentages are by weight except where stated otherwise, and in which the ratio of parts by weight to parts by volume is that of the kilogram to the liter.

EXAMPLES

Butadiene (6.5 parts), water (5 parts by volume) and the carbon dioxide, catalyst and solvent specified in the following tables were added to an autoclave which was pressurised with oxygen to 6.5 bar (gauge) and heated at 100° to 20 hours. The reaction mixture was found to contain the amount of 2-butene-1,4-diol specified.

TABLE 1
EXAMPLES 1–8

| Example No. | Catalyst and amount (parts) | | Solvent and amount (parts by vol.) | | Carbon Dioxide (parts) | Yield of 2-butene-1,4-diol (parts) | % Conversion of butadiene to 2-butene-1,4-diol |
|---|---|---|---|---|---|---|---|
| 1 | cuprous bromide | 0.25 | acetone | 25 | 2 | 1.4 | 14 |
|   | copper bronze | 0.25 | Crotyl phenyl-sulphide | 5 | | | |
| 2 | cuprous bromide | 0.25 | acetone | 5 | 2 | 0.15 | 1.4 |
|   | copper bronze | 0.25 | | | | | |
| 3 | cupric acetate | 0.25 | acetone | 5 | 1 | 0.58 | 5.8 |
|   | copper bronze | 0.25 | Crotyl phenyl-sulphide | 0.5 | | | |
| 4 | cupric acetate | 0.25 | acetone | 25 | 1 | 1.1 | 10 |
|   | copper bronze | 0.25 | Crotyl phenyl-Sulphide | 2 | | | |
| 5 | cupric acetate | 0.25 | acetone | 8 | 1 | 0.52 | 5.2 |
|   | cupric bronze | 0.25 | Triphenyl thio-phosphite | 0.5* | | | |
| 6 | cupric acetate | 0.25 | acetone | 25 | 1 | 0.65 | 6.4 |
|   | cuprous trifluoromethane sulphonate | 0.1 | | | | | |
| 7 | cupric acetate | 0.25 | Isopropanol | 20 | 1 | 0.15 | 1.5 |
|   | cuprous trifluoromethane sulphonate | 0.1 | | | | | |
| 8 | cupric acetate | 0.25 | Isopropanol | 20 | Nil | 0.01 | — |
|   | Cuprous Trifluoromethane sulphonate | 0.1 | | | | | |

*parts by weight

TABLE 2
EXAMPLES 9–18

| Example No. | Catalyst and amount (parts) | | Solvent and amount (parts by vol.) | | Carbon Dioxide (parts) | Yield of 2-butene-1,4-diol (parts) |
|---|---|---|---|---|---|---|
| 9 | Co(II)acetate | 0.25 | t-butanol | 15 | 1 | 0.6 |
| 10 | Mn(II)acetate | 0.25 | t-butanol | 15 | 1 | 0.31 |
| 11 | Nickel acetate | 0.25 | t-butanol | 15 | 1 | 0.58 |
| 12 | Molybdenum hexacarbonyl | 0.25 | t-butanol | 15 | 1 | 0.31 |
| 13 | Cr(III)acetoacetonate | 0.25 | Isopropanol | 15 | 1 | 0.2 |
| 14 | Cr(III)acetoacetonate | 0.25 | Acetone | 15 | 1 | 0.81 |
| 15 | Cr(III)acetoacetonate | 0.25 | t-butanol | 15 | 1 | 0.93 |
| 16 | Cr(III)acetoacetonate | 0.25 | Acetonitrile | 10 | 1 | 0.61 |
| 17 | Cr(III)acetoacetonate | 0.25 | Acetonitrile | 15 | 1 | 1.1 |
|    | lithium hydroxide | 0.25 | (time of reaction 8 hr at 100° C.) | | | |
| 18 | Cr(III)acetoacetonate | 0.25 | Acetonitrile (conditions as Ex. 17) | 15 | Nil | 0.37 |
|    | lithium hydroxide | 0.25 | | | | |

We claim:

1. A process for the manufacture of 2-butene-1,4-diol which comprises reacting butadiene with water and oxygen in the presence of a copper, nickel, cobalt, chromium, manganese or molybdenum catalyst.

2. A process according to claim 1 which is carried out in the presence of carbon dioxide.

3. A process according to claim 2 in which the amount of carbon dioxide is 0.01 to 0.5 mols carbon dioxide per mole of butadiene.

4. A process according to claim 1 in which at least 1 mole of water is used per mole of butadiene.

5. A process according to claim 1 in which the catalyst is an inorganic salt or an organic acid salt.

6. A process according to claim 1 in which lithium hydroxide is present.

7. A process according to claim 1 which is carried out in the liquid phase in the presence of a solvent.

8. A process according to claim 1 which is carried out at a temperature in the range 50° to 150° C.

9. A process according to claim 1 in which the process is carried out in the liquid phase at a temperature in the range 50° to 150° C. in a solvent selected from the group consisting of lower aliphatic alcohols, lower aliphatic ketones and lower alkyl cyanides in the presence of lithium hydroxide and, as catalyst, of copper, nickel, cobalt, chromium, manganese, molybdenum halide or salt of an aliphatic carboxylic acid containing up to 20 carbon atoms.

10. A process according to claim 9 in which carbon dioxide is also present.